US009061025B2

(12) United States Patent
Burstein et al.

(10) Patent No.: US 9,061,025 B2
(45) Date of Patent: Jun. 23, 2015

(54) METHODS FOR SELECTING HEADACHE PATIENTS RESPONSIVE TO BOTULINUM TOXIN THERAPY

(75) Inventors: Rami Burstein, Chestnut Hill, MA (US); Catherine C. Turkel, Newport Coast, CA (US); Mitchell F. Brin, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 1083 days.

(21) Appl. No.: 11/513,794

(22) Filed: Aug. 31, 2006

(65) Prior Publication Data

US 2008/0057084 A1 Mar. 6, 2008

(51) Int. Cl.
*A61K 39/08* (2006.01)
*A61K 38/48* (2006.01)
*A61K 9/00* (2006.01)
*C07K 14/33* (2006.01)

(52) U.S. Cl.
CPC .................................. *A61K 38/4893* (2013.01)

(58) Field of Classification Search
None
See application file for complete search history.

(56) References Cited

U.S. PATENT DOCUMENTS

| | | | |
|---|---|---|---|
| 5,437,291 A | 8/1995 | Pasricha et al. | 128/898 |
| 5,670,484 A | 9/1997 | Binder | 514/14 |
| 5,714,468 A * | 2/1998 | Binder | 424/780 |
| 5,766,605 A | 6/1998 | Sanders et al. | 424/239.1 |
| 5,989,545 A | 11/1999 | Foster et al. | 424/183.1 |
| 6,063,768 A | 5/2000 | First | 514/14 |
| 6,139,845 A | 10/2000 | Donovan | 424/236.1 |
| 6,299,893 B1 | 10/2001 | Schwartz et al. | 424/422 |
| 6,306,423 B1 | 10/2001 | Donovan et al. | 424/423 |
| 6,312,708 B1 | 11/2001 | Donovan | 424/423 |
| 6,358,917 B1 * | 3/2002 | Carruthers et al. | 514/2 |
| 6,423,319 B1 | 7/2002 | Brooks et al. | 424/239.1 |
| 6,447,787 B1 | 9/2002 | Gassner | 424/247.1 |
| 6,458,365 B1 | 10/2002 | Aoki | |
| 6,464,986 B1 | 10/2002 | Aoki et al. | 424/239.1 |
| 6,623,742 B2 | 9/2003 | Voet | 514/2 |
| 6,776,992 B2 | 8/2004 | Aoki | |
| 6,787,517 B1 * | 9/2004 | Gil et al. | 514/1 |
| 6,838,434 B2 | 1/2005 | Voet | |
| 8,241,641 B2 * | 8/2012 | Blumenfeld | 424/239.1 |
| 8,889,151 B2 * | 11/2014 | Turkel et al. | 424/247.1 |
| 8,936,790 B2 * | 1/2015 | Turkel et al. | 424/239.1 |
| 2003/0224019 A1 | 12/2003 | O'Brien | 424/247.1 |
| 2005/0191320 A1 | 9/2005 | Turkel et al. | |
| 2005/0191321 A1 | 9/2005 | Turkel et al. | |
| 2006/0104995 A1 | 5/2006 | Turkel et al. | |
| 2006/0121057 A1 | 6/2006 | Turkel et al. | |
| 2012/0040911 A1 * | 2/2012 | Blumenfeld | 514/18.3 |
| 2012/0245096 A1 * | 9/2012 | Blumenfeld | 514/18.3 |

FOREIGN PATENT DOCUMENTS

| | | | | |
|---|---|---|---|---|
| DE | 101 50 415 A1 | 5/2003 | ............. | A61K 35/70 |
| WO | WO 03/011333 | 2/2003 | ............. | A61K 31/18 |

OTHER PUBLICATIONS

J. MacW. et al (S.A. Medical Journal, Apr. 10, 1971).*
MacW MacGregor et al (S.A. Medical Journal, Apr. 10, 1971).*
Krymchantowski et al (Arq Neuropsiquiatr, Dec. 1999;, 57(40:990-3)(Abstract only).*
MacGregor et al (S.A. Medical Journal, Apr. 10, 1971).*
http://abc news.go.com/WNT/story, Mar. 8, 2006 in view of Binder (U.S. Patent No. 5,714,468 issued Feb. 3, 1998).*
U.S. Appl. No. 60/418,789, filed Oct. 15, 2002.
U.S. Appl. No. 10/194,805, filed Jul. 11, 2002.
U.S. Appl. No. 10/731,973, filed Dec. 9, 2003.
U.S. Appl. No. 10/423,380, filed Apr. 15, 2003.
U.S. Appl. No. 10/630,587, filed Jul. 29, 2003.
U.S. Appl. No. 10/752,869, filed Jan. 18, 2005.
Aoki K., et al, *Mechanisms of the antinociceptive effect of subcutaneous Botox: Inhibition of peripheral and central nociceptive processing*, Cephalalgia Sep. 2003;23(7):649.
Aoki, K., et al., *Botulinum toxin type A and other botulinum toxin serotypes: a comparative review of biochemical and pharmacological actions*, Eur J. Neurol 2001: (suppl 5); 21-29.
Aoki, K., *Physiology and pharmacology of therapeutic botulinum neurotoxins*, in Kreyden, O., editor, Hyperhydrosis and botulinum toxin in dermatology, Basel, Karger; 2002; 30: pp. 107-116.
Bhattacharya K., et al., *Novel uses of botulinum toxin type A: two case reports*, Mov Disord 2000; 15(Suppl 2):51-52.
Bigalke H., et al., *Botulinum A Neurotoxin Inhibits Non-Cholinergic Synaptic Transmission in Mouse Spinal Cord Neurons in Culture*, Brain Research 360;318-324:1985.
Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316;244-251:1981.
Boyd R.S. et al., Mov Disord, 10(3):376:1995.
Brin, M., et al., *Botulinum toxin type A: pharmacology*, in Mayer N., editor, Spasticity: etiology, evaluation, management and the role of botulinum toxin, 2002; pp. 110-124.

(Continued)

Primary Examiner — Nita M Minnifield
(74) Attorney, Agent, or Firm — Brigitte C. Phan; Ted A. Chan; Debra D. Condino

(57) ABSTRACT

A method for treating a headache by selecting a patient determined to be responsive to administration of a botulinum neurotoxin for treatment of a headache by determining that the patient has or has a propensity to have an imploding headache and/or an ocular headache pain and administering a botulinum toxin to the patient, thereby treating the headache. A method for selecting from a population of patients with headache or with a propensity to have a headache, those patients whose headache will respond to administration of a botulinum neurotoxin by identifying from a population of patients with headache or with a propensity to have a headache those patients who have or who have a propensity to have an imploding headache pain and/or an ocular headache pain.

5 Claims, 4 Drawing Sheets

(56) References Cited

OTHER PUBLICATIONS

Bushara K., *Botulinum toxin and rhinorrhea*, Otolaryngol Head Neck Surg 1996;114(3):507.
Crnac, M., et al., *Individual injection scheme in the treatment of headache with botulinum toxin*, J Neurol 2004;251(Suppl 1):I/43 A9.
Cui, M., et al., *Mechanisms of the antinociceptive effect of subcutaneous BOTOX®: inhibition of peripheral and central nociceptive processing*, Naunyn Schmiedebergs Arch Pharmacol 2002; 365 (supp 2): R17.
Gonelle-Gispert, C., et al., *SNAP-25a and -25b isofors are both expressed in insulin-secreting cells and can function in insulin secretion*, Biochem J 1;1999, 339 (pt 1):159-165.
Guyton A.C. et al., *Textbook of Medical Physiology*, W.B. Saunders Company 1996, ninth edition, pp. 686-688.
Habermann E., et al., *Tetanus Toxin and Botulinum A and C Neurotoxins Inhibit Noradrenaline Release From Cultured Mouse Brain*, J Neurochem 51(2);522-527:1988.
Habermann E., *Inhibition by Tetanus and Botulinum A Toxin of the release of [$^3$H]Noradrenaline and [$^3$H]GABA From Rat Brain Homogenate*, Experientia 44;224-226:1988.
Habermann, Naunyn-Schmiedeberg's Arch. Pharmacol. 1974; 281, 47-56.
*Harrison's Principles of Internal Medicine* (1998), edited by Anthony Fauci et al., 14$^{th}$ edition, published by McGraw Hill.
Jahanshahi M., et al., *Psychological functioning before and after treatment of torticollis with botulinum toxin*, J Neurol Neurosurg Psychiatry 1992; 55(3): 229-231.
Jankovic J. et al., *Therapy With Botulinum Toxin*, Marcel Dekker, Inc., (1994), p. 5.
Jankovic J., et al *Therapy With Botulinum Toxin*, Marcel Dekker, Inc., (1994), p. 150.
Katsambas A., et al., *Cutaneous diseases of the foot: Unapproved treatments*, Clin Dermatol Nov.-Dec. 2002;20(6):689-699.
Kriegler J., et al., *Single site Botox(TM) injection: Effective treatment for migraine headaches*, Headache May 2006;46(5):849.
LaButta R., et al., *Effectiveness of botulinum toxin type-A in the treatment of migraine headache: A randomized controlled trial*, Neurology Mar. 2005;64(Suppl 1).
Li Y, et al., *Sensory and motor denervation influences epidermal thickness in rat foot glabrous skin*, Exp Neurol 1997;147:452-462.
Marjama-Jyons, J., et al., *Tremor-Predominant Parkinson's Disease*, Drugs & Aging 16(4);273-278:2000.
Moyer E et al., *Botulinum Toxin Type B: Experimental and Clinical Experience*, being chapter 6, pp. 71-85 of "Therapy With Botulinum Toxin", edited by Jankovic, J. et al. (1994), Marcel Dekker, Inc.
Murry T., et al., *Spasmodic dysphonia; emotional status and botulinum toxin treatment*, Arch Otolaryngol Mar. 1994; 120(3): 310-316.
Naumann M., et al., *Botulinum toxin type A in the treatment of focal, axillary and palmar hyperhidrosis and other hyperhidrotic conditions*, European J. Neurology 6 (Supp 4): S111-S115:1999.
Pearce, L.B., *Pharmacologic Characterization of Botulinum Toxin for Basic Science and Medicine*, Toxicon 35(9);1373-1412.
Ragona, R.M., et al., *Management of parotid sialocele with botulinum toxin*, The Laryngoscope, 1999, 109:1344-1346.
Rogers J., et al., *Injections of botulinum toxin A in foot dystonia*, Neurology Apr. 1993;43 (4 Suppl 2).
Sanchez-Prieto, J., et al., *Botulinum Toxin A Blocks Glutamate Exocytosis From Guinea Pig Cerebral Cortical Synaptosomes*, Eur J. Biochem 165;675-681:1987.
Schantz, E.J., et al, *Properties and use of Botulinum toxin and Other Microbial Neurotoxins in Medicine*, Microbiol Rev. 56;80-99:1992.
Sevim, S., et al., *Botulinum toxin-A therapy for palmar and plantar hyperhidrosis*, Acta Neurol Belg Dec. 2002;102(4):167-70.
Singh, *Critical Aspects of Bacterial Protein Toxins*, pp. 63-84 (chapter 4) of Natural Toxons II, edited by B.R. Singh et al., Plenum Press, New York (1976).
Suputtitada, A., *Local botulinum toxin type A injections in the treatment of spastic toes*, Am J Phys Med Rehabil Oct. 2002;81(10):770-5.

Tacks, L., et al., *Idiopathic toe walking: Treatment with botulinum toxin A injection*, Dev Med Child Neurol 2002; 44 (Suppl 91):6.
Weigand et al, *Naunyn-Schmiedeberg's Arch. Pharmacol*. 1976; 292, 161-165.
BOTOX®, Product Information Sheet (2006).
Dysport: Product Information (2005).
MYOBLOC, Information Sheet (2004).
Aoki KR. Evidence for antinociceptive activity of botulinum toxin type A in pain management. Headache 2003;43 Suppl 1:S9-15.
Aoki KR. Pharmacology and immunology of botulinum toxin serotypes. J Neurol 2001;248 Suppl 1:Jan. 3-10.
Bigal ME, Sheftell FD, Rapoport AM, et al. Chronic daily headache in a tertiary care population: correlation between International Headache Society diagnostic criteria and proposed revisions of criteria for chronic daily headache. Cephalalgia 2002;22:432-438.
Binder WJ, Brin MF, Blitzer A. Botulinum toxin type A (BOTOX) for treatment of migraine headaches: an open-label study. Otolaryngol Head Neck Surg 2000;123(6):669-676.
Binz T. et al., *The Complete Sequence of Botulinum Neurotoxin Type A and Comparison with Other Clostridial Neurotoxins*, J Biological Chemistry 265(16);9153-9158:1990.
Blugerman G., et al., *Multiple eccrine hidrocystomas: A new therapeutic option with botulinum toxin*, Dermatol Surg May 2003;29(5):557-9.
Blumenfeld AM, Dodick DW, Silberstein SD. Botulinum neurotoxin for the treatment of migraine and other primary headache disorders. Dermatol Clin 2004;22:167-175.
Blumenfeld AM. Botulinum toxin type A as an effective prophylactic treatment in primary headache disorders. Headache 2003;43:853-860.
Brandes JL, Saper JR, Diamond M, et al. Topiramate for migraine prevention: a randomized controlled trial. JAMA;2004;291:965-973.
Brem, H., et al, *Placebo-Controlled Trial of Safety and Efficacy of Intraoperative Controlled Delivery by Biodegradable Polymers of Chemotherapy for Recurrent Gliomas*, Lancet 345;1008-1012:1995.
Brin MF, Fahn S, Moskowitz C, et al. Localized injections of botulinum toxin for the treatment of focal dystonia and hemifacial spasm. Movement Dis 1987;2:237-254.
Brin MF, Swope DM, O'Brien C, et al. BOTOX® for migraine: double-blind, placebo-controlled, region-specific evaluation. Cephalalgia 2000;20:421-422.
Castillo JP, Munoz P, Guitera V, et al. Epidemiology of chronic daily headache in the general population. Headache 1999;39:190-196.
Cheshire WP, Abashian SW, Mann JD. Botulinum toxin in the treatment of myofascial pain syndrome. Pain 1994;59:65-69.
Colas R, Munoz P, Temprano R, et al. Chronic daily headache with analgesic overuse: epidemiology and impact on quality of life. Neurology 2004;62:1338-1342.
Couch JR. Placebo effect and clinical trials in migraine therapy. Meth Prob Migraine Trials, Neuroepid 1987;6:178-185.
Cui M, Khanijou S, Rubino J, et al. Subcutaneous administration of botulinum toxin A reduces formalin-induced pain. Pain 2004;107:125-133.
Dabrowski et al.; *Botulinum toxin as a novel treatment for self mutilation in Lesch-Nyhan syndrome*, Ann Neurol Sep. 2002;52(3 Suppl 1):S157.
Depakote® ER (package insert). Abbott Laboratories; 2003.
Dowson, A.J., et al., *Managing Chronic Headaches in the Clinic*, Int J. Clin Pract., Dec. 2004, 58, 12, pp. 1142-1151.
Duggan et al.; A surbey of Botulinum neurotoxin substrate expression in cells; Mov Disord, 10(3):376:1995.
Durham PL, Cady Ryan, Cady Roger. Regulation of calcitonin gene-related peptide secretion from trigeminal nerve cells by botulinum toxin type A: implications for migraine therapy. Headache 2004;44:35-42.
European Agency for the Evaluation of Medicinal Products. Note for guidance on clinical investigation of medicinal products for the treatment of migraine. Dec. 2003.
Foster L, Clapp L, Erickson M, Jabbari B. Botulinum toxin A and chronic low back pain. A randomized, double-blind study. Neurol 2001;56:1290-1293.
Freund BJ, Schwartz M. Use of botulinum toxin in chronic whiplash-associated disorder. Clin J Pain 2002;18(6 Suppl):S163-S168.

(56) References Cited

OTHER PUBLICATIONS

Fung L. K. et al., *Pharmacokinetics of Interstitial Delivery of Carmustine 4-Hydroperoxycyclophosphamide and Paclitaxel From a Biodegradable Polymer Implant in the Monkey Brain*, Cancer Research 58;672-684:1998.
Gladstone JP., Gawel M. *Newer formulations of the triptans: advances in migraine management*, Drugs. 2003;63(21):2285-305.
Gladstone, J., et al., *Chronic Daily Headache: A Rational Approach to a Challenging Problem*, Seminars in Neurology, 2003, vol. 23, No. 3, pp. 265-275.
Gonelle-Gispert et al.; snap-25a and -25b isoforms are both expressed in insulin-secreting cells and can function in insulin secretion;*Biochem J 1*;339 (pt 1):159-65:1999.
Headache Classification Committee of the International Headache Society. Classification and diagnostic criteria for headache disorders, cranial neuralgias and facial pain. Cephalalgia 1988;8 Suppl 7:1-96.
Headache Classification Subcommittee of the International Headache Society. The international classification of headache disorders, $2^{nd}$ ed. Cephalalgia 2004;24 Suppl 1:1-151.
Heckmann M., et al., *Botulinum toxin type A injection in the treatment of lichen simplex: An open pilot study*, J Am Acad Dermatol Apr. 2002;46(4):617-9.
Hering R, Gardiner I, Catarci T, Witmarch T, Steiner T, de Belleroche J. Cellullar adaptation in migraineurs with chronic daily headache. Cephalalgia 1993;13:261-6.
Holroyd KA, Stensland M, Lipchik GL, et al. Psychosocial correlates and impact of chronic tension-type headaches. Headache 2000; 40:3-16.
International Headache Society committee on Clinical Trials in Migraine. Guidelines for controlled trials of drugs in migraine. First edition. Cephalalgia 1991;11:1-12.
Jacks, L., et al., *Idiopathic toe walking: Treatment with botulinum toxin A injection*, Dev Med Child Neurol 2002;44(Suppl 91):6).
Jost W., *Ten years' experience with botulinum toxin in anal fissure*, Int J Colorectal Dis Sep. 2002;17(5):298-302.
Klapper JA, Mathew NT, Klapper A et al. Botulinum toxin type A (BTX-A) for the prophylaxis of chronic daily headache. Cephalalgia 2000;20:292-293.
Linde M, Limmroth V, Dahlöf C, on behalf of the Headache Masters Programme. Ethical aspects of placebo in migraine research. Cephalalgia 2003;23:491-495.
Linton-Dahlöf, M Linde, Dahlöf C. Withdrawal therapy improves chronic daily headache associated with long-term misuse of headache medication: a retrospective study. Cephalalgia 2000;20:658-662.
Lipton RB, Bigal ME. Chronic daily headache: is analgesic overuse a cause or a consequence? Neurology 2003;61:154-155.
Lipton RB, Stewart WF. Migraine headaches: epidemiology and comorbidity. Clin Neuroscience 1998;5:2-9.
Loder, E., et al., *Use of Botulinum Toxins for Chronic Headaches: A Focused Review*, The Clinical Journal of Pain, 2002, 18, pp. S169-S176.
Maizels, M., et al., *The Patient with Daily Headaches*, American Family Physician, Dec. 2004, vol. 70, No. 12, pp. 2299-2306.
Manzoni GC, Granella F, Sandrini G, et al. Classification of chronic daily headache by International Headache Society criteria: limits and new proposals. Cephalalgia 1995;15:37-43.
Mathew N, Kaup A, Kailasam J. Botulinum toxin type A modifies chronic migraine further long-term (3years) experience with up to ten sets of treatments. Headache 2003;43:576.
Mathew NT, Reuveni U, Perez F. Transformed or evolutive migraine Headache 1987;27:102-106.
Mauskop A. Botulinum toxin in the treatment of chronic daily headaches. Cephalalgia 1999;19:453.
Monzon MJ, Lainez MJA. Quality of life in migraine and chronic daily headache patients. Cephalalgia 1998;18:638-643.
O'Brien PC, Fleming TR. A multiple testing procedure for clinical trials. Biometrics 1979;35:549-556.
Ondo WG, Vuong KD, Derman HS. Botulinum toxin A for chronic daily headache: a randomized, placebo-controlled, parallel design study. Cephalalgia 2004;24:60-5.
Payne M., et al, *Botulinum toxin as a novel treatment for self mutilation in Lesch-Nyhan syndrome*, Ann Neurol Sep. 2002;52(3 Supp 1):S157.
Purkiss J, Welch M, Doward S, et al. Capsaicin-stimulated release of substance P from cultured dorsal root ganglion neurons: involvement of two distinct mechanisms. Biochem Pharmacol 2000;59:1403-1406.
Rahimtoola H, Buurma H, Tijssen CC, et al. Migraine prophylactic medication usage patterns in The Netherlands. Cephalalgia 2003;23:293-301.
Relja G, Granato A, Maria Antonello R, Zorzon M. *Headache induced by chronic substance use: analysis of medication overused and minimum dose required to induce headache*, Headache. Feb. 2004;44(2):148-53.
Rogers J., et al., *Injections of botulinum toxin A in foot dystonia*, Neurology Apr. 1993;43(4 Suppl 2).
Saper JR, Lake AE III, Cantrell DT, et al. Chronic daily headache prophylaxis with tizanidine: a double-blind, placebo-controlled, multicenter outcome study. Headache 2002;42:470-482.
Scher AI, Stewart WF, Liberman J, et al. Prevalence of frequent headache in a population sample. Headache 1998;38:497-506.
Schim, J, et al., *Effect of Preventive Treatment with Botulinum Toxin Type A on Acute Headache Medication Usage in Migraine Patients*, Current Medical Research Opinions, vol. 20, No. 1, 2004, pp. 49-53.
Schwartz BS, Stewart WF, Lipton RB. Loss of workdays and decreased work effectiveness associated with headache in the workplace. J Occup Environ Med 1997;39:320-327.
Siegel S. Non-parametric statistics for the behavioral sciences. New York: McGraw-Hill Book Company, 1956:96:116-127.
Silberstein SD, Lipton RB, Sliwinski M. Classification of daily and near-daily headaches: field trial of revised IHS criteria. Neurology 1996;47:871-875.
Silberstein SD, Lipton RB, Solomon S, Mathew NT. Classification of daily and near-daily headaches: proposed revisions to the IHS criteria. Headache 1994;34:1-7.
Silberstein SD, Lipton RB. Chronic daily headache, including transformed migraine, chronic tension-type headache, and medication overuse. In: Silberstein SD, Lipton RB, Dalessio DJ, eds. Wolff's headache and other head pain, $7^{th}$ ed. New York, NY: Oxford University Press;2001:247-282.
Silberstein SD, Lipton RB. Chronic daily headache. Curr Opin Neurol 2000;13:277-283.
Silberstein SD, Neto W, Schmitt J, et al. Topiramate in migraine prevention. Arch Neurol 2004;61:490-495.
Silberstein SD, Silberstein MM. New concepts in the pathogenesis of headache. Part II. Pain Man 1990;3:334-342.
Silvestrini M, Bartolini M, Coccia M, et al. Topiramate in the treatment of chronic migraine. Cephalalgia 2003;23:820-824.
Sloop RR, Cole BA, Escutin RO. Reconstituted botulinum toxin type A does not lose potency in humans if it is refrozen or refrigerated for 2 weeks before use. Neurology. Jan. 1997;48(1):249-53.
Smuts JA, Baker MK, Smuts HM, et al. Prophylactic treatment of chronic tension-type headache using botulinum toxin type A. Eur J Neurol 1999;6(Suppl 4):S99-S102.
Solomon GD, Sokbieranda FG, Genzen JR. Quality of life assessment among migraine patients treated with Sumatriptan. Headache 1995;35:449-454.
Spira PJ, Beran RG. Gabapentin in the prophylaxis of chronic daily headache: a randomized, placebo-controlled study. Neurology 2003;61:1753-1759.
Stewart WF, Lipton RB, Celentano DD, et al. Prevalence of migraine headaches in the United States. Relation to age, income, race and other sociodemographic factors. JAMA 1992;267:64-69.
Tepper, S., et al., *Botulinum Toxin Type A in the Preventive Treatment of Refractory Headaches—Comparison Between Medication Overusers and Nonmedication Overusers Groups*, Cephalalgia, 2003, 23, p. 715, poster P5N86.
Troost BT. Botulinum toxin type A (Botox) in the treatment of migraine and other headaches. Expert Rev Neurotherap 2004;4:27-31.

(56) References Cited

OTHER PUBLICATIONS

Wang SJ, Fuh JL, Lu SR, et al. Chronic daily headache in Chinese elderly: prevalence, risk factors and biannual follow-up. Neurology 2000;54:314-319.

Wang SJ, Fuh JL, Lu SR, et al. Quality of life differs among headache diagnoses: analysis of SF-36 survey in 901 headache patients. Pain 2001;89:285-292.

Welch KM, Goadsby PJ. Chronic daily headache: nosology and pathophysiology. Curr Opin Neurol 2002;15:287-95. Review.

Wissel J, Muller J, Dressnandt J, Heinen F, Naumann M, Topka H, Poewe W. Management of spasticity associated pain with botulinum toxin A. J Pain Symptom Manage 2000;20:44-9.

Woolf C. et al., *Neuropathic Pain: Aetiology, Symptoms, Mechanisms, and Management*, Lancet 1999; 353: 1959-64.

\* cited by examiner

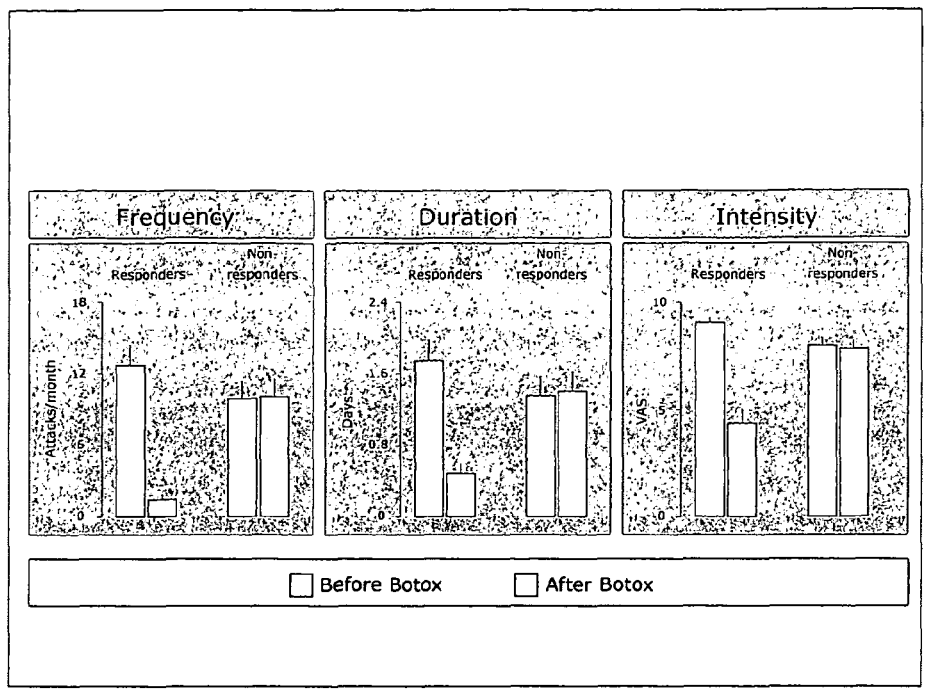
Figure 1. Effects of a botulinum toxin type A (Botox) on frequency, duration and pain intensity of migraine in responders vs. non-responders.

Figure 2. Illustration of possible mechanism to explain prophylactic action of a botulinum toxin to treat migraine by blockade of extracranial nerves relaying sensory signals from the meninges, bone and scalp.

Figure 3 Illustration of Botulinum toxin injection sites for treatment of headache.

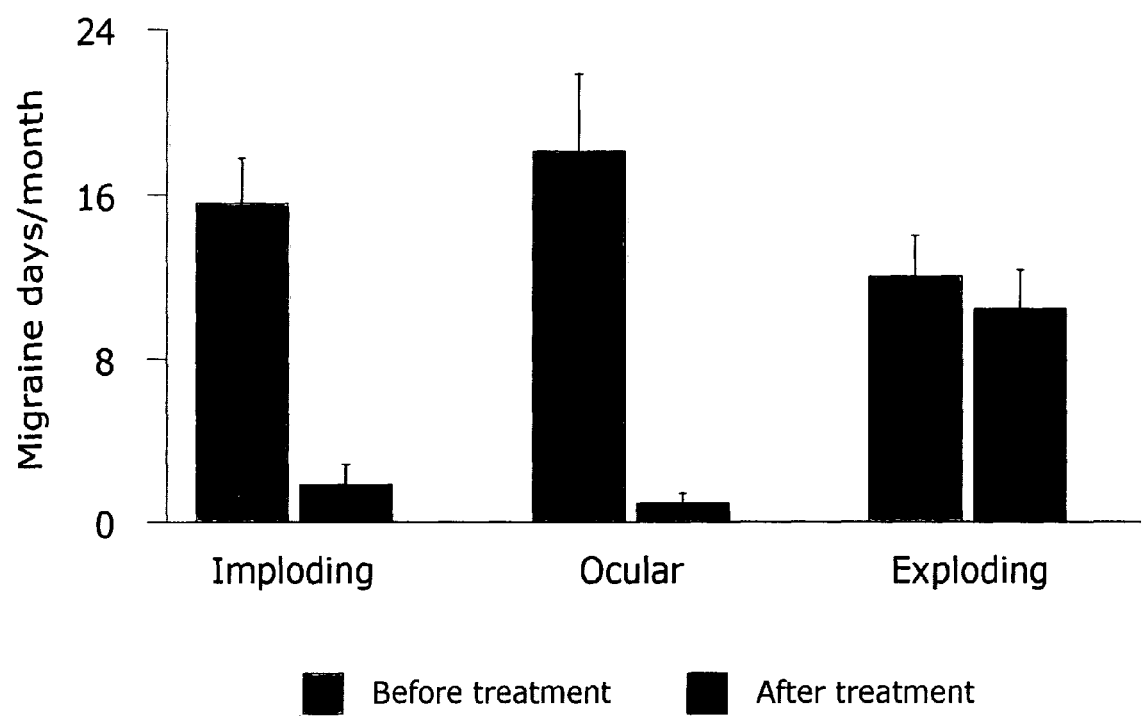
Figure 4. Effect of Botulinum toxin type A administration on the number of migraine days per month in migraine patients with imploding, ocular or exploding headache pain headache.

METHODS FOR SELECTING HEADACHE PATIENTS RESPONSIVE TO BOTULINUM TOXIN THERAPY

BACKGROUND

The present invention relates to methods for selecting a patient responsive to a headache treatment and to methods for treating a headache. In particular, the present invention relates to methods for selecting a patient responsive to treatment of a headache with a botulinum toxin and to methods for treating a headache with a botulinum toxin.

A headache is a pain in the head, such as in the scalp, face, forehead or neck. A headache can be a primary headache or a secondary headache. A primary headache is a headache that is not caused by another condition. Contrarily, a secondary headache is due to a disease or medical condition, such as an illness, infection, injury, stroke or other abnormality. Thus, with a secondary headache there is an underlying disorder that produces the headache as a symptom of that underlying disorder. Tension headache is the most common type of primary headache and tension headaches account for about 90% of all headaches. A tension headache is often experienced in the forehead, in the back of the head and neck, or in both regions. It has been described as a tight feeling, as if the head were in a vise. Soreness in the shoulders or neck is common. Nausea is uncommon with a tension headache.

Migraine headaches are recurrent headaches that may be unilateral or bilateral. Migraine headaches may occur with or without a prodrome. The aura of a migraine may consist of neurologic symptoms, such as dizziness, tinnitus, scotomas, photophobia, or visual scintillations (eg, bright zigzag lines). Migraines without aura are the most common, accounting for more than 80% of all migraines.

An estimated 10-20% of the population suffers from migraine headaches. An estimated 6% of men and 15-17% of women in the United States have migraine. Migraines most commonly are found in women, with a 3:1 female-to-male ratio.

About 2% of all headaches are secondary headaches. For example, a cervicogenic headache is a headache which is due to a neck problem, such as an abnormality of neck muscles, which can result from prolonged poor posture, arthritis, injuries of the upper spine, or from a cervical spine disorder. Sinus headache is another type of secondary headache. A sinus headache can be caused by inflammation and/or infection in the paranasal sinuses.

An ocular headache (i.e. opthalmoplegic migraine) presents with a lateralized pain (often around the eye) often accompanied by nausea, vomiting, and double vision. With ocular headache visual disturbances are common and can include visual hallucinations, such as sparks, light flashes, zigzags of light or visual field defects. The patient can report pain or pressure on or in his eyes. An ocular headache pain is a pain which is localized in or around the eye.

A headache (such as a migraine headache) can be accompanied by an exploding headache pain. An exploding headache pain has the seminal diagnostic characteristic of perception by the patient of a pressure or force being exerted within the skull (that is within the head) in an outward fashion. The patient can report that it feels as if his head is going to explode, as if his head will split open, and/or that it feels as if someone is stabbing him inside his head. Thus, in an exploding headache the pain is perceived by the patient as a type of pain that moves from the inside to the outside of the head. Contrarily, a headache (such as a migraine headache) can be accompanied by an imploding headache pain. An imploding headache pain has the seminal diagnostic characteristic of perception by the patient of a pressure or force being exerted from outside of the skull in an inward fashion. The patient can report that it feels as if something heavy is sitting on his head (such as on his forehead), as if something is squeezing his head, as if something is tightening a vice on his head, and/or as if a sharp object is being inserted into his head. Thus, in an imploding headache the pain is perceived by the patient as a type of pain that moves from the outside to the inside of the head.

Botulinum Toxin

The genus *Clostridium* includes more than one hundred and twenty seven species, grouped according to their morphology and functions. The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (purified neurotoxin complex)[1] is a $LD_{50}$ in mice (i.e. 1 unit). One unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63-84 (chapter 4) of Natural Toxins II, edited by B. R. Singh et al., Plenum Press, New York (1976) (where the stated $LD_{50}$ of botulinum toxin type A of 0.3 ng equals 1 U is corrected for the fact that about 0.05 ng of BOTOX® equals 1 unit). One unit (U) of botulinum toxin is defined as the $LD_{50}$ upon intraperitoneal injection into female Swiss Webster mice weighing 18 to 20 grams each.

[1] Available from Allergan, Inc., of Irvine, Calif. under the tradename BOTOX® in 100 unit vials)

Seven generally immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Moyer E et al., *Botulinum Toxin Type B: Experimental and Clinical Experience*, being chapter 6, pages 71-85 of "Therapy With Botulinum Toxin", edited by Jankovic, J. et al. (1994), Marcel Dekker, Inc. Botulinum toxin apparently binds with high affinity to cholinergic motor neurons, is translocated into the neuron and blocks the release of acetylcholine. Additional uptake can take place through low affinity receptors, as well as by phagocytosis and pinocytosis.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc ($Zn^{++}$) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotype A and E cleave SNAP-25. Botulinum toxin serotype $C_1$ was originally thought to cleave syntaxin, but was found to cleave syntaxin and SNAP-25. Each of the botulinum toxins specifically cleaves a different bond, except botulinum toxin type B (and tetanus toxin) which cleave the same bond. Each of these cleavages block the process of vesicle-membrane docking, thereby preventing exocytosis of vesicle content.

Botulinum toxins have been used in clinical settings for the treatment of neuromuscular disorders characterized by hyperactive skeletal muscles (i.e. motor disorders). In 1989 a botulinum toxin type A complex has been approved by the U.S. Food and Drug Administration for the treatment of blepharospasm, strabismus and hemifacial spasm. Subsequently, a botulinum toxin type A was also approved by the FDA for the treatment of cervical dystonia and for the treatment of glabellar lines, and a botulinum toxin type B was approved for the treatment of cervical dystonia. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months, although significantly longer periods of therapeutic activity have been reported.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. *Biochem J* 1; 339 (pt 1):159-65:1999, and *Mov Disord,* 10(3):376:1995 (pancreatic islet B cells contains at least SNAP-25 and synaptobrevin).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ is apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain*, J Neurochem 51 (2); 522-527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165; 675-681:1987. Thus, when adequate concentrations are used, stimulus-evoked release of most neurotransmitters is blocked by botulinum toxin. See e.g. Pearce, L. B., *Pharmacologic Characterization of Botulinum Toxin For Basic Science and Medicine*, Toxicon 35(9); 1373-1412 at 1393; Bigalke H., et al., *Botulinum A Neurotoxin Inhibits Non-Cholinergic Synaptic Transmission in Mouse Spinal Cord Neurons in Culture*, Brain Research 360; 318-324:1985; Habermann E., *Inhibition by Tetanus and Botulinum A Toxin of the release of*

[³H]Noradrenaline and [³H]GABA From Rat Brain Homogenate, Experientia 44; 224-226:1988, Bigalke H., et al., Tetanus Toxin and Botulinum A Toxin Inhibit Release and Uptake of Various Transmitters, as Studied with Particulate Preparations From Rat Brain and Spinal Cord, Naunyn-Schmiedeberg's Arch Pharmacol 316; 244-251:1981, and; Jankovic J. et al., Therapy With Botulinum Toxin, Marcel Dekker, Inc., (1994), page 5.

Botulinum toxin type A can be obtained by establishing and growing cultures of Clostridium botulinum in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of Clostridium botulinum with characteristics of $\geq 3 \times 10^7$ U/mg, an $A_{260}/A_{278}$ of less than 0.60 and a distinct pattern of banding on gel electrophoresis. The known Shantz process can be used to obtain crystalline botulinum toxin type A, as set forth in Shantz, E. J., et al, Properties and use of Botulinum toxin and Other Microbial Neurotoxins in Medicine, Microbiol Rev. 56; 80-99:1992. Generally, the botulinum toxin type A complex can be isolated and purified from an anaerobic fermentation by cultivating Clostridium botulinum type A in a suitable medium. The known process can also be used, upon separation out of the non-toxin proteins, to obtain pure botulinum toxins, such as for example: purified botulinum toxin type A with an approximately 150 kD molecular weight with a specific potency of $1-2 \times 10^8$ $LD_{50}$ U/mg or greater; purified botulinum toxin type B with an approximately 156 kD molecular weight with a specific potency of $1-2 \times 10^8$ $LD_{50}$ U/mg or greater, and; purified botulinum toxin type F with an approximately 155 kD molecular weight with a specific potency of $1-2 \times 10^7$ $LD_{50}$ U/mg or greater.

Botulinum toxins and/or botulinum toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo. Pure botulinum toxin can also be used to prepare a pharmaceutical composition.

As with enzymes generally, the biological activities of the botulinum toxins (which are intracellular peptidases) is dependant, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can stabilized with a stabilizing agent such as albumin and gelatin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of Clostridium botulinum grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below $-5°$ C. BOTOX® can be reconstituted with sterile, non-preserved saline prior to intramuscular injection. Each vial of BOTOX® contains about 100 units (U) of Clostridium botulinum toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks. Sloop, Neurology, 48:249-53:1997.

It has been reported that botulinum toxin type A has been used in clinical settings as follows:
(1) about 75-125 units of BOTOX® per intramuscular injection (multiple muscles) to treat cervical dystonia;
(2) 5-10 units of BOTOX® per intramuscular injection to treat glabellar lines (brow furrows) (5 units injected intramuscularly into the procerus muscle and 10 units injected intramuscularly into each corrugator supercilii muscle);
(3) about 30-80 units of BOTOX® to treat constipation by intrasphincter injection of the puborectalis muscle;
(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.
(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:
(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

Additionally, intramuscular botulinum toxin has been used in the treatment of tremor in patients with Parkinson's disease, although it has been reported that results have not been impressive. Marjama-Jyons, J., et al., *Tremor-Predominant Parkinson's Disease*, Drugs & Aging 16(4); 273-278:2000.

It is known that botulinum toxin type A can have an efficacy for up to 12 months (*European J. Neurology* 6 (Supp 4): S111-S1150:1999), and in some circumstances for as long as 27 months, when used to treat glands, such as in the treatment of hyperhydrosis. See e.g. Bushara K., *Botulinum toxin and rhinorrhea*, Otolaryngol Head Neck Surg 1996; 114(3):507, and *The Laryngoscope* 109:1344-1346:1999. However, the usual duration of an intramuscular injection of Botox® is typically about 3 to 4 months.

The success of botulinum toxin type A to treat a variety of clinical conditions has led to interest in other botulinum toxin serotypes. Two commercially available botulinum type A preparations for us in humans are BOTOX® available from Allergan, Inc., of Irvine Calif., and DYSPORT® available from Beaufour Ipsen, Porton Down, England. A botulinum toxin type B preparation (MYOBLOC®) is available from Elan Pharmaceuticals of San Francisco, Calif.

In addition to having pharmacologic actions at the peripheral location, botulinum toxins may also have inhibitory effects in the central nervous system. Work by Weigand et al, *Naunyn-Schmiedeberg's Arch. Pharmacol.* 1976; 292, 161-165, and Habermann, *Naunyn-Schmiedeberg's Arch. Pharmacol.* 1974; 281, 47-56 showed that botulinum toxin is able to ascend to the spinal area by retrograde transport. As such, a botulinum toxin injected at a peripheral location, for example intramuscularly, may be retrograde transported to the spinal cord.

U.S. Pat. No. 5,989,545 discloses that a modified clostridial neurotoxin or fragment thereof, preferably a botulinum toxin, chemically conjugated or recombinantly fused to a particular targeting moiety can be used to treat pain by administration of the agent to the spinal cord.

It has been reported that use of a botulinum toxin to treat various spasmodic muscle conditions can result in reduced depression and anxiety, as the muscle spasm is reduced. Murry T., et al., *Spasmodic dysphonia; emotional status and botulinum toxin treatment*, Arch Otolaryngol 1994 March; 120(3): 310-316; Jahanshahi M., et al., *Psychological functioning before and after treatment of torticollis with botulinum toxin*, J Neurol Neurosurg Psychiatry 1992; 55(3): 229-231. Additionally, German patent application DE 101 50 415 A1 discusses intramuscular injection of a botulinum toxin to treat depression and related affective disorders.

A botulinum toxin has also been proposed for or has been used to treat skin wounds (U.S. Pat. No. 6,447,787), various autonomic nerve dysfunctions (U.S. Pat. No. 5,766,605), post-operative pain and visceral pain (U.S. Pat. No. 6,464,986), neuralgia pain (U.S. patent application Ser. No. 630,587), hair growth and hair retention (U.S. Pat. No. 6,299,893), dental related ailments (U.S. provisional patent application Ser. No. 60/418,789), fibromyalgia (U.S. Pat. No. 6,623,742), various skin disorders (U.S. patent application Ser. No. 10/731,973), motion sickness (U.S. patent application Ser. No. 752,869), psoriasis and dermatitis (U.S. Pat. No. 5,670,484), injured muscles (U.S. Pat. No. 6,423,319) various cancers (U.S. Pat. No. 6,139,845), smooth muscle disorders (U.S. Pat. No. 5,437,291), down turned mouth corners (U.S. Pat. No. 6,358,917), nerve entrapment syndromes (U.S. patent application 2003 0224019), various impulse disorders (U.S. patent application Ser. No. 423,380), acne (WO 03/011333) and neurogenic inflammation (U.S. Pat. No. 6,063,768). Controlled release toxin implants are known (see e.g. U.S. Pat. Nos. 6,306,423 and 6,312,708) as is transdermal botulinum toxin administration (U.S. patent application Ser. No. 10/194,805).

Botulinum toxin type A has been used to treat epilepsia partialis continua, a type of focal motor epilepsy. Bhattacharya K., et al., *Novel uses of botulinum toxin type A: two case reports*, Mov Disord 2000; 15(Suppl 2):51-52.

Additionally, a botulinum toxin may have an effect to reduce induced inflammatory pain in a rat formalin model. Aoki K., et al, *Mechanisms of the antinociceptive effect of subcutaneous Botox: Inhibition of peripheral and central nociceptive processing*, Cephalalgia 2003 September; 23(7): 649. Furthermore, it has been reported that botulinum toxin nerve blockage can cause a reduction of epidermal thickness. Li Y, et al., *Sensory and motor denervation influences epidermal thickness in rat foot glabrous skin*, Exp Neurol 1997; 147:452-462 (see page 459). Finally, it is known to administer a botulinum toxin to the foot to treat excessive foot sweating (Katsambas A., et al., *Cutaneous diseases of the foot: Unapproved treatments*, Clin Dermatol 2002 November-December; 20(6):689-699; Sevim, S., et al., *Botulinum toxin-A therapy for palmar and plantar hyperhidrosis*, Acta Neurol Belg 2002 December; 102(4):167-70), spastic toes (Suputtitada, A., *Local botulinum toxin type A injections in the treatment of spastic toes*, Am J Phys Med Rehabil 2002 October; 81(10):770-5), idiopathic toe walking (Tacks, L., et al., *Idiopathic toe walking: Treatment with botulinum toxin A injection*, Dev Med Child Neurol 2002; 44(Suppl 91):6), and foot dystonia (Rogers J., et al., *Injections of botulinum toxin A in foot dystonia*, Neurology 1993 April; 43(4 Suppl 2)).

Furthermore, a botulinum toxin has been used to treat many types of headache, such as tension headache, (see eg U.S. Pat. No. 6,458,365), migraine headache pain (see eg U.S. Pat. No. 5,714,468), and sinus headache (see U.S. Pat. No. 6,838,434). When a patient who has a headache or who has a propensity to have a headache is administered a botulinum toxin (to treat the headache and/or to prevent occurrence of a headache) the patient can respond to the administered botulinum toxin in varying ways, meaning that the botulinum toxin can be totally effective, partially effective or not effective at all to treat the headache and/or to prevent occurrence of a headache. Clearly it could benefit patient care, conserve physician time and prevent unnecessary use of a pharmaceutical if it could be determined prior to administration of a botulinum toxin if use of the botulinum for a particular patient will be effective to treat a headache and/or to prevent development of a headache.

What is needed therefore is a method for determining prior to administration of a botulinum toxin to a patient who has a headache or who has a propensity to have a headache, if the botulinum toxin will be effective in that patient.

SUMMARY

The present invention meets this need and provides methods for determining prior to administration of a botulinum toxin to a patient who has a headache or who has a propensity to have a headache if the botulinum toxin will be effective in that patient.

The following definitions apply herein:

"About" means "that the item, parameter or term so qualified encompasses a range of plus or minus ten percent above and below the value of the stated item, parameter or term.

"Alleviating" means a reduction in the occurrence of a pain, of a headache pain. Thus, alleviating includes some reduction, significant reduction, near total reduction, and total reduction. An alleviating effect may not appear clinically for between 1 to 7 days after administration of a botulinum toxin to a patient.

"Botulinum toxin" means a neurotoxin produced by *Clostridium botulinum*, as well as modified, recombinant, hybrid and chimeric botulinum toxins. A recombinant botulinum toxin can have the light chain and/or the heavy chain thereof made recombinantly by a non-Clostridial species. "Botulinum toxin," as used herein, encompasses the botulinum toxin serotypes A, B, C, D, E, F and G. "Botulinum toxin," as used herein, also encompasses both a botulinum toxin complex (i.e. the 300, 600 and 900 kDa complexes) as well as pure botulinum toxin (i.e. the about 150 kDa neurotoxic molecule), all of which are useful in the practice of the present invention. "Purified botulinum toxin" means a pure botulinum toxin or a botulinum toxin complex that is isolated, or substantially isolated, from other proteins and impurities which can accompany the botulinum toxin as it is obtained from a culture or fermentation process. Thus, a purified botulinum toxin can have at least 90%, preferably more than 95%, and most preferably more than 99% of the non-botulinum toxin proteins and impurities removed. The botulinum $C_2$ and $C_3$ cytotoxins, are not botulinum neurotoxins, and are excluded from the scope of the present invention.

An "exploding headache" or "exploding headache pain" is a headache that is perceived by the patient as being or as including a pain from the inside to the outside of the patient's head.

An "imploding headache" or "imploding headache pain" is a headache that is perceived by the patient as being or as including a pain from the outside to the inside of the patient's head.

"Local administration" means administration (i.e. by a subcutaneous, intramuscular, subdermal or transdermal route) of a pharmaceutical agent to or to the vicinity of a muscle or of a subdermal location or in the head of a patient by a non-systemic route. Thus, local administration excludes systemic (i.e. to the blood circulation system) routes of administration, such as intravenous or oral administration. Peripheral administration means administration to the periphery (i.e. to a location on or within a limb, trunk or head of a patient) as opposed to a visceral or gut (i.e. to the viscera) administration.

"Treating" means to alleviate (or to eliminate) at least one symptom of a headache pain either temporarily or permanently.

A patient "free of headache" after administration of a botulinum toxin means that the patient does not experience a headache for at least a two week period after administration of the botulinum toxin.

A patient "partially free of headache" after administration of a botulinum toxin means that the patient experiences a less than 50% reduction in headache present days after administration of the botulinum toxin. For example, if prior to administration of a botulinum toxin the patient experienced headache on six days in a two week period and after administration of the botulinum toxin the patient experiences headache on four days in a two week period, that patient can be said to be partially free of headache after administration of the botulinum toxin.

A patient "substantially free of headache" after administration of a botulinum toxin means that the patient experiences a greater than 50% reduction in headache present days after administration of the botulinum toxin. For example, if prior to administration of a botulinum toxin the patient experienced headache on six days in a two week period and after administration of the botulinum toxin the patient experiences headache on two days in a two week period, that patient can be said to be substantially free of headache after administration of the botulinum toxin.

"Modified botulinum toxin" means a botulinum toxin that has had at least one of its amino acids deleted, modified, or replaced, as compared to a native botulinum toxin. Additionally, the modified botulinum toxin can be a recombinantly produced neurotoxin, or a derivative or fragment of a recombinantly made neurotoxin. A modified botulinum toxin retains at least one biological activity of the native botulinum toxin, such as, the ability to bind to a botulinum toxin receptor, or the ability to inhibit neurotransmitter release from a neuron. One example of a modified botulinum toxin is a botulinum toxin that has a light chain from one botulinum toxin serotype (such as serotype A), and a heavy chain from a different botulinum toxin serotype (such as serotype B). Another example of a modified botulinum toxin is a botulinum toxin coupled to a neurotransmitter, such as substance P.

Our invention includes a method for treating a headache by selecting a patient determined to be responsive to administration of a botulinum neurotoxin for treatment of a headache by determining that the patient has or has a propensity to have an imploding and/or ocular headache pain, and administering a botulinum toxin to the selected patient thereby treating the headache. The botulinum neurotoxin used can be a botulinum toxin type A, B, C, D, E, F or G. Preferably, the botulinum toxin is a botulinum toxin type A. The botulinum neurotoxin can be administered in an amount of between about 1 unit and about 10,000 units.

The botulinum toxin administration can be by a local administration, such as an intramuscular or subcutaneous administration to a location on or within a head of a patient, to a facial muscle of the patient and or to a forehead of the patient. The local administration of the botulinum toxin can be to a subdermal location or to a muscle location from which the patient perceives a pain to arise. The headache treated by our invention can be a migraine headache.

Our invention also encompasses a method for treating a migraine headache by selecting a patient determined to be responsive to administration of a botulinum neurotoxin for treatment of a migraine headache by determining that the patient has or has a propensity to have an imploding and/or ocular headache pain, followed by local administration of between about 1 unit and about 1,500 units of a botulinum toxin type A to the patient, thereby treating the migraine headache, Administration of the botulinum toxin can be by a transdermal route (i.e. by application of a botulinum toxin in a cream, patch or lotion vehicle), subdermal route (i.e. subcutaneous or intramuscular), or intradermal route of administration. Additionally, the botulinum toxin can be administered as a monotherapy or in conjunction with other medications, such as a triptan.

The dose of a botulinum toxin used according to the present invention is preferably less than the amount of a botulinum toxin that would be used to paralyze a muscle, since an intent of administration of a botulinum toxin according to the present invention is not to paralyze a muscle but to reduce a pain sensory output from sensory neurons located in or on a muscle, or in or under the skin.

Our invention also includes a method for improving a responsiveness of a patient to a treatment of a headache with a botulinum neurotoxin by identifying a patient who has or has a propensity to have an imploding and/or ocular headache pain, and administering a botulinum neurotoxin to the patient, thereby treating the headache, wherein the identification of the patient with an imploding and/or ocular headache is predictive of increased responsiveness to the treatment of headache with the botulinum neurotoxin.

Another embodiment of our invention is a method for identifying a patient with increased responsiveness to treatment of a headache with a botulinum neurotoxin by screening a population of patients to identify those patients who have or who have a propensity to have an imploding and/or ocular headache pain, wherein the identification of a patient who has or has a propensity to have an imploding headache is predictive of increased responsiveness to the treatment of a headache pain with a botulinum neurotoxin.

Finally, our invention includes a method for selecting from a population of patients with headache or with a propensity to have a headache, those patients whose headache will respond to administration of a botulinum neurotoxin by identifying from a population of patients with headache or with a propensity to have a headache those patients who have or who have a propensity to have an imploding and/or ocular headache pain.

Botulinum toxin type A is a preferred botulinum toxin. The botulinum toxin can be administered in an amount of between about 1 unit and about 3,000 units. The local administration of the botulinum toxin can be to or to a vicinity of where the patient experiences or is predisposed to experience pain. Alternately, the local administration can be by intramuscular injection or to a subdermal location from which the patient perceives the existence of a pain to arise, typically at the forehead.

DRAWINGS

The following drawings are presented to assist understanding of aspects and features of the present invention.

FIG. 1 is a bar graph which show the effects of a botulinum toxin type A (i.e. BOTOX®) administration on frequency, duration and pain intensity of migraine in responders vs. non-responders.

FIG. 2 is a diagram which illustrates a possible effect on extracranial nerves as a mechanism of action to explain how a botulinum toxin (such as BOTOX) can treat migraine.

FIG. 3 is two anatomical diagrams showing locations for intramuscular injections of a botulinum toxin for a treatment of migraine.

FIG. 4 is a bar graph which shows the effects of botulinum toxin type A (BOTOX®) administration on the number of migraine days per month in migraine patients with imploding, ocular or exploding headache pain headache.

DESCRIPTION

The present invention is based on the discovery that a headache such as a migraine headache can be by treated by selecting for patients with imploding headache (i.e. an outside to inside pain perception) and/or ocular headache (as opposed to selecting patients with exploding headache (i.e. an inside to outside pain perception). Concomitantly, the present invention is based on the discovery that a headache such as a migraine headache can be by treated by selecting for treatment those patients who do not predominantly have or who do not have at all an exploding headache (i.e. an inside to outside pain perception).

We have found that patients who have imploding and/or ocular headache pain respond well to treatment with a botulinum toxin, whereas patients who have exploding headache do not respond well to treatment with a botulinum toxin.

A patient with a headache (such as a migraine headache) for whom administration of a botulinum toxin results in alleviation of a symptom (such as a pain symptom) of the headache can be referred to as a responder. Similarly, a patient with a propensity or a predisposition to experience headaches (such as migraine headaches) for whom administration of a botulinum toxin results in a prophylactic reduction in the number, duration and/or intensity of the headaches experiences can also referred to as a responder.

A patient with a headache (such as a migraine headache) for whom administration of a botulinum toxin does not result in a significant or substantial alleviation of a symptom (such as a pain symptom) of the headache can be referred to as a non-responder. Similarly, a patient with a propensity or a predisposition to experience headaches (such as migraine headaches) for whom administration of a botulinum toxin does not result in a significant or substantial prophylactic reduction in the number, duration and/or intensity of the headaches experiences can also referred to as a non-responder.

Thus, as shown by FIG. 1, patients can respond very differently to administration of a botulinum toxin (such as Botox) to treat a migraine headache, depending upon whether the patient is a responder or a non-responder. Clearly, a patient that is a non-responder should not be administered a botulinum toxin to treat a headache because to do so provides medication to which the patient will not respond to or to which he will respond poorly. Such unnecessary medication can be potentially injurious to the patient's health, as well as amounting to a waste of medication and physician time.

It is important to note that the method of administration of a botulinum toxin (including the characteristics of fixed site dose, follow the pain dosing, multiple sites, single site, high dose or low dose) are not important or significant characteristics of our invention. The significant characteristic of our invention is to select (for administration of a botulinum toxin to treat a headache and/or to prevent development of a headache) for a patient who has an imploding headache and not select a patient who has an exploding headache. We have found that a patient who has an imploding headache pain show a greater reduction in headache pain and/or in the number of headache free days (upon administration of a botulinum toxin using a fixed site dose, follow the pain dosing, multiple sites, single site, high dose or low dose of the botulinum toxin) than will a patient who has an exploding headache pain.

A headache can be treated by local administration of a therapeutically effective amount of a botulinum toxin. Thus, a botulinum toxin (such as a botulinum toxin serotype A, B, $C_1$, D, E, F or G) can be injected (i.e. intramuscular injection) into or in the vicinity where a patient is experiencing the pain to thereby suppress the pain or prevent its occurrence. Alternately, the botulinum toxin can be administered to an intradermal or subdermal pain sensory neuron thereby suppressing and treating a headache.

We have developed a method for treating a patient with a headache with a botulinum toxin with a high probability that the patient will respond to the botulinum toxin, that is that a symptom of his headache will be alleviated. This treatment method is base upon a method for selecting for treatment patients who are responders. According to our invention, patients who are determined to be non-responders are not administered a botulinum toxin to treat their headache.

Responders are selected for by determining if the patient has an imploding headache or an exploding headache. We found that in a group of 34 patients with imploding headache 32 (91%) responded to administration of a botulinum toxin. On the other hand in a separate group of 27 patient with exploding headache we found that 24 (92%) did not respond to administration of the botulinum toxin. Thus, we determined that patients with imploding headache are responders, whereas patients with exploding headache are non-responders.

Various injection techniques can be used to treat a headache with a botulinum toxin. For example single or multiple injections have been used. Additionally, the botulinum toxin injection can be at a fixed site or sites or a "follow the pain" (injections tailored to the sites where the patient perceives the pain to arise from). See eg. Kriegler J., et al., *Single site Botox™ injection: Effective treatment for migraine headaches*, Headache 2006 May; 46(5):849; LaButta R., et al., *Effectiveness of botulinum toxin type-A in the treatment of migraine headache: A randomized controlled trial*, Neurology 2005 March; 64(Suppl 1), and; Crnac, M., et al., *Individual injection scheme in the treatment of headache with botulinum toxin*, J Neurol 2004; 251 (Suppl 1):I/43 A9.

For example, a botulinum toxin can be administered intramuscularly in an average of up to 20 separate injections to each patient. The botulinum toxin can be administered at up to seven different muscles (i.e. 20 total injections into 7 muscles). From example, about 100 to 300 units of a botulinum toxin such as BOTOX can be administered to a patient.

The botulinum toxin (i.e. Botox) can be administered (23-58 injections of 105-260 units in 6-7 muscle areas) determined based on the pain distribution pattern and the severity of pain in the particular muscle area of the patient. The patient can be injected in one or more of 6 muscle areas; frontal/glabellar, occipitalis, temporalis, semispinalis, splenius capitis, and trapezius muscles, as shown in Table 1 and the FIG. 3.

TABLE 1

| Preferred Dose and Injection Sites | | | |
|---|---|---|---|
| Muscle Area | Number of Units | Bilateral Injection | Total Dose (Botox U) |
| Frontal/Glabellar | 25-40 | No | 25-40 |
| Occipitalis | 10 | Yes | 20 |
| Temporalis | 10-25 | Yes | 20-50 |
| Masseter (optional) | 0-25 | Yes | 0-50 |

TABLE 1-continued

| Preferred Dose and Injection Sites | | | |
|---|---|---|---|
| Muscle Area | Number of Units | Bilateral Injection | Total Dose (Botox U) |
| Trapezius | 10-30 | Yes | 20-60 |
| Semispinalis | 5-10 | Yes | 10-20 |
| Splenius capitis | 5-10 | Yes | 10-20 |
| Total Dose Range | | | 105-260 |

Administration of a botulinum toxin to a head, neck or shoulder location may act to block extracranial nerves which act to rely sensory (pain) signals from the meninges, bone and scalp to a central (CNS) location, as illustrate by FIG. 2. Thus, it is known that muscles have a complex system of innervation and sensory output. Thus, anterior motor neurons located in each segment of the anterior horns of the spinal cord gray matter give rise to efferent alpha motor neurons and efferent gamma motor neurons that leave the spinal cord by way of the anterior roots to innervate skeletal (extrafusal) muscle fibers. The alpha motor neurons cause contraction of extrafusal skeletal muscle fibers while the gamma motor neurons innervate the intrafusal fibers of skeletal muscle. As well as excitation by these two types of efferent anterior motor neuron projections, there are additional, afferent sensory neurons which project from muscle spindle and golgi tendon organs and act to transmit information regarding various muscle parameter status to the spinal cord, cerebellum and cerebral cortex. These efferent motor neurons which relay sensory information from the muscle spindle include type Ia and type II sensory afferent neurons. See e.g. pages 686-688 of Guyton A. C. et al., *Textbook of Medical Physiology*, W.B. Saunders Company 1996, ninth edition.

Significantly, it has been determined that a botulinum toxin can act to reduce transmission of sensory information from muscle type la afferent neurons. Aoki, K., *Physiology and pharmacology of therapeutic botulinum neurotoxins*, in Kreyden, O., editor, Hyperhydrosis and botulinum toxin in dermatology, Basel, Karger; 2002; 30: pages 107-116, at 109-110. And it has been hypothesized that botulinum toxin can have a direct effect upon muscle cell sensory afferents and modify signals from these afferents to the central nervous system. See e.g. Brin, M., et al., *Botulinum toxin type A: pharmacology*, in Mayer N., editor, Spasticity: etiology, evaluation, management and the role of botulinum toxin, 2002; pages 110-124, at 112-113; Cui, M., et al., *Mechanisms of the antinociceptive effect of subcutaneous BOTOX®: inhibition of peripheral and central nociceptive processing*, Naunyn Schmiedebergs Arch Pharmacol 2002; 365 (supp 2): R17; Aoki, K., et al., *Botulinum toxin type A and other botulinum toxin serotypes: a comparative review of biochemical and pharmacological actions*, Eur J. Neurol 2001: (suppl 5); 21-29. Thus, it has been demonstrated that botulinum toxin can cause an altered sensory output from muscle to CNS and brain.

Importantly, the sensory neurons from which afferent output is to be inhibited by a method according to the present invention need not be located on or within a muscle, but can be in an intradermal or subdermal location.

Thus, pain can be due to sensory input from afferent facial area neurons. Administration of a botulinum toxin to a facial muscles or skin to reduce sensory output from the muscle can result in alleviation of and prevention of pain.

Our invention also includes a method for treating an ocular headache, such as an ocular migraine headache by administration of a botulinum toxin by infusing the botulinum toxin behind the globe of the eye to target C and A-delta pain fibers present in this peri-bulbar location in the skull, thereby following the neural innervation.

The amount of the botulinum toxin administered according to a method within the scope of the disclosed invention can vary according to the particular characteristics of the pain being treated, including its severity and other various patient variables including size, weight, age, and responsiveness to therapy. To guide the practitioner, typically, no less than about 1 unit and no more than about 70 units of a botulinum toxin type A (such as BOTOX® is administered per injection site (i.e. to each muscle portion injected), per patent treatment session. For a botulinum toxin type A such as DYSPORT®, no less than about 4 units and no more about 280 units of the botulinum toxin type A are administered per injection site, per patent treatment session. For a botulinum toxin type B such as MYOBLOC®, no less than about 40 units and no more about 2800 units of the botulinum toxin type B are administered per injection site, per patent treatment session. Less than about 1, 4 or 40 units (of BOTOX®, DYSPORT® and MYOBLOC® respectively) can fail to achieve a desired therapeutic effect, while more than about 70, 280 or 2800 units (of BOTOX®, DYSPORT® and MYOBLOC® respectively) can result in significant muscle hypotonicity, weakness and/or paralysis.

More preferably: for BOTOX® no less than about 5 units and no more about 60 units of a botulinum toxin type A; for DYSPORT® no less than about 20 units and no more than about 240 units, and; for MYOBLOC®, no less than about 200 units and no more than about 2400 units are, respectively, administered per injection site, per patent treatment session.

Most preferably: for BOTOX® no less than about 10 units and no more about 50 units of a botulinum toxin type A; for DYSPORT® no less than about 40 units and no more than about 200 units, and; for MYOBLOC®, no less than about 400 units and no more than about 2000 units are, respectively, administered per injection site, per patent treatment session. It is important to note that there can be multiple injection sites (i.e. a pattern of injections) for each patient treatment session.

Generally, the total amount of BOTOX®, DYSPORT® or MYOBLOC®, suitable for administration to a patient according to the methods of the invention disclosed herein should not exceed about 300 units, about 1,500 units or about 15,000 units respectively, per treatment session. For XEOMIN® (a 150 kDa botulinum toxin type A formulation available from Merz Pharmaceuticals, Potsdam, Germany) about 1× to about 2× the amounts of BOTOX® set forth above can be used in each instance.

When BOTOX® is administered, each vial of BOTOX® contains 100 units of *Clostridium botulinum* toxin type A (purified), 0.5 mg albumin (human), and 0.9 mg sodium chloride in a sterile, vacuum-dried form without a preservative. One unit corresponds to the calculated median lethal intraperitoneal dose ($LD_{50}$) in mice. Preferably, the vials are stored in a freezer between −20° C. and −5° C. before use. Reconstitution is with 0.9% sterile saline (without preservatives) for injection.

Examples of Clostridial toxins within the scope of the present invention include neurotoxins made by *Clostridium botulinum*, *Clostridium butyricum* and *Clostridium beratti* species. In addition, the botulinum toxins used in the methods of the invention may be a botulinum toxin selected from a group of botulinum toxin types A, B, C, D, E, F, and G. In one embodiment of the invention, the botulinum neurotoxin administered to the patient is botulinum toxin type A. Botulinum toxin type A is desirable due to its high potency in humans, ready availability, and known use for the treatment of skeletal and smooth muscle disorders when locally administered by intramuscular injection. The present invention also includes the use of (a) Clostridial neurotoxins obtained or processed by bacterial culturing, toxin extraction, concentration, preservation, freeze drying, and/or reconstitution; and/or (b) modified or recombinant neurotoxins, that is neurotoxins that have had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made. These neurotoxin variants retain the ability to inhibit neurotransmission between or among neurons, and some of these variants may provide increased durations of inhibitory effects as compared to native neurotoxins, or may provide enhanced binding specificity to the neurons exposed to the neurotoxins. These neurotoxin variants may be selected by screening the variants using conventional assays to identify neurotoxins that have the desired physiological effects of inhibiting neurotransmission.

Botulinum toxins for use according to the present invention can be stored in lyophilized, vacuum dried form in containers under vacuum pressure or as stable liquids. Prior to lyophilization the botulinum toxin can be combined with pharmaceutically acceptable excipients, stabilizers and/or carriers, such as albumin. The lyophilized material can be reconstituted with saline or water to create a solution or composition containing the botulinum toxin to be administered to the patient.

Although the composition may only contain a single type of neurotoxin, such as botulinum toxin type A, as the active ingredient to suppress neurotransmission, other therapeutic compositions may include two or more types of neurotoxins, which may provide enhanced therapeutic treatment of a headache. For example, a composition administered to a patient may include botulinum toxin type A and botulinum toxin type B. Administering a single composition containing two different neurotoxin's may permit the effective concentration of each of the neurotoxins to be lower than if a single neurotoxin is administered to the patient while still achieving the desired therapeutic effects. The composition administered to the patient may also contain other pharmaceutically active ingredients, such as, protein receptor or ion channel modulators, in combination with the neurotoxin or neurotoxins. These modulators may contribute to the reduction in neurotransmission between the various neurons. For example, a composition may contain gamma aminobutyric acid (GABA) type A receptor modulators that enhance the inhibitory effects mediated by the $GABA_A$ receptor.

The botulinum neurotoxin may be administered by any suitable method as determined by the attending physician. The methods of administration permit the neurotoxin to be administered locally to a selected target tissue. Methods of administration include injection of a solution or composition containing the neurotoxin, as described above, and include implantation of a controlled release system that controllably releases the neurotoxin to the target tissue. Such controlled release systems reduce the need for repeat injections. Diffusion of biological activity of a botulinum toxin within a tissue appears to be a function of dose and can be graduated. Jankovic J., et al *Therapy With Botulinum Toxin*, Marcel Dekker, Inc., (1994), page 150. Thus, diffusion of botulinum toxin can be controlled to reduce potentially undesirable side effects that may affect the patient's cognitive abilities. For example, the neurotoxin can be administered so that the neurotoxin primarily effects neural systems believed to be involved in the generation of pain and/or inflammation, and does not have negatively adverse effects on other neural systems.

Local administration of a botulinum toxin, can provide a high, local therapeutic level of the toxin. A controlled release polymer capable of long term, local delivery of a Clostridial toxin to a target muscle permits effective dosing of a target tissue. A suitable implant, as set forth in U.S. Pat. No. 6,306,423 entitled "Neurotoxin Implant", allows the direct introduction of a chemotherapeutic agent to a target tissue via a controlled release polymer. The implant polymers used are preferably hydrophobic so as to protect the polymer incorporated neurotoxin from water induced decomposition until the toxin is released into the target tissue environment.

Local administration of a botulinum toxin, according to the present invention, by injection or implant to a target tissue provides a superior alternative to systemic administration of pharmaceuticals to patients to alleviate a headache.

The amount of a botulinum toxin selected for local administration to a target tissue according to the present disclosed invention can be varied based upon criteria such as the severity of the pain or type of headache being treated, the extent of muscle tissue to be treated, solubility characteristics of the neurotoxin toxin chosen as well as the age, sex, weight and health of the patient. For example, the extent of the area of muscle tissue influenced is believed to be proportional to the volume of neurotoxin injected, while the quantity of the suppressant effect is, for most dose ranges, believed to be proportional to the concentration of a botulinum toxin administered. Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., $14^{th}$ edition, published by McGraw Hill).

EXAMPLES

The following non-limiting example provides those of ordinary skill in the art with specific preferred selection and treatment methods within the scope of the present invention and are not intended to limit the scope of the invention. In the following examples various modes of non-systemic administration of a Clostridial neurotoxin can be carried out. For example, by intramuscular injection, subcutaneous injection or by implantation of a controlled release implant.

Example 1

Use of a Botulinum Toxin to Treat the Migraine of a Patient with Imploding Headache Pain A female patient, 48 years old complained of migraine headaches since the age of 12 and reported migraine family history. Before botulinum toxin administration she suffered 20 migraine attacks a month, each lasting a day with pain intensity of 7 on a scale of 0 to 10. She described the pain as feeling "like a very tight band across my forehead", which was viewed as an outside to the inside the head pain, and she was therefore classified as having an imploding headache pain. The patient can be administered various doses of a botulinum toxin at various injection sites. For example, BOTOX® can be administered at a dose of about 5 Units at multiple (32) sites into the frontalis, glabellar, temporalis, occipitalis, splenius capitus, semispinalis, trapezius muscle groups for to a total dose of about 160 Units. After BOTOX® administration the patient experienced only one migraine attack a month with a pain intensity of 3 on a scale of 0 to 10.

A botulinum toxin type B, C, D, E, F or G can be substituted for the botulinum toxin type A used above.

Example 2

Selecting Migraine Patients with Imploding Headache Pain Versus Exploding Headache Pain for Treatment with Botulinum Toxin Seven patients with migraine headache who responded to administration of a botulinum toxin to treat their migraine and seven additional patients with migraine did not respond or who responded poorly to administration of a botulinum toxin to treat their migraine were included in this study. Significantly, it was determined through patent interviews that the non-responders were all patients who reported that their migraine included exploding headache pain (that is reported a perception by the patient of having an inside to outside headache pain) with little or no imploding headache pain, and that the responders were all patients who reported that their migraine included imploding headache pain (that is reported a perception by the patient of having an outside to inside headache pain) with little or no exploding headache pain.

Each patient was administered a botulinum toxin type A (BOTOX®). The patients can be administered various doses of a botulinum toxin at various injection sites. For example, about 5 units of BOTOX® can be injected into injection sites in the frontalis, glabellar, temporalis, occipitalis, splenius capitus, semispinalis, and trapezius muscle groups. The total dose per patient can be between about 180 and about 220 Units. The results are shown in Table 1, where "Change in HA Frequency Month" means the change in how many days a month the patient has a headache after botulinum toxin administration; an arrow means there was a change to the number of days a month with headache to the number shown to the right of the arrow. "HA Duration (Days)" means how long each headache lasts. "Change in Pain Intensity" means the intensity of the headache pain as perceived by the patients on a scale of 0 to 10. "NC" means no change.

As shown by Table 2, most non-responders did not have a change in monthly headache frequency, duration of headache or pain intensity after botulinum toxin administration. As also shown by Table 1, most responders did have a change in monthly headache frequency, duration of headache or pain intensity after botulinum toxin administration.

TABLE 2

Comparison of effect of Effect of BOTOX ® on Non-Responders Versus Responders

| Non-Responders | | | |
|---|---|---|---|
| Patient | Change in HA Frequency/ Month | HA Duration (Days) | Change in Pain Intensity |
| 1 | NC | NC | NC |
| 2 | 3 → 2 | 5 → 3 | NC |
| 3 | NC | NC | NC |
| 4 | NC | NC | NC |
| 5 | NC | NC | NC |
| 6 | NC | NC | NC |
| 7 | NC | NC | 7 → 3 |

TABLE 2-continued

Comparison of effect of Effect of BOTOX ® on
Non-Responders Versus Responders

Responders

| Patient | HA Frequency/ Month | HA Duration (Days) | Change in HA Intensity |
|---|---|---|---|
| 8 | 8 → 0 | NC | NC |
| 9 | 30 → 0 | NC | NC |
| 10 | 12 → 4* | NC | 10 → 5 |
| 11 | 8 → 2 | 3 → 1 | NC |
| 12 | 30 → 4 | 6 → 2 | NC |
| 13 | 30 → 30 | NC | 10 → 9 |
| 14 | 4 → 1 | 3 → 1 | 7 → 5 |

Example 3

Further Study Regarding Selecting Migraine Patients with Imploding Headache Pain Versus Exploding Headache Pain for Treatment with Botulinum Toxin We carried out a study to identify neurological symptoms that would tag episodic-migraine patients who respond prophylactically to a botulinum toxin type A treatment. Quite a few migraine patients have noticed a considerable decrease in attack frequency following botulinum toxin injections. Some migraineurs (patients with migraine) however do not experience such improvement after a botulinum toxin type A administration. This study determined a marker that can tease out prospective responders from non-responders.

Patients were interviewed in the clinic for detailed migraine symptoms and medical history. Patients experiencing a >75% reduction in attack frequency within 3 months of botulinum toxin type A treatment were selected as responders. Patients who showed no change in attack frequency were selected as non-responders. The interviewer had no knowledge of the patient's response to the botulinum toxin type A treatment before the interview was completed.

Responders (n=35) experienced significant drops in the number of attacks/month (12.7±1.7 before botulinum toxin type A vs. 1.5±0.4 after treatment), attack duration (1.7±0.2 vs. 0.5±0.1 days), and headache intensity (9.1±0.2 vs. 4.4±0.6 pain score). Non-responders (n=24) yielded identical values before and after treatment: 10.5±1.6 vs. 10.7±1.6 attacks/month; 1.4±0.2 vs. 1.4±0.2 days/attack; 8.0±1.4 vs. 7.8±0.4 pain score. No difference was found between responders and non-responders across the full array of the classic migraine symptoms. However, there was one clear difference between the two groups: 92% of non-responders described their headache as exploding (extreme pressure inside the head) whereas 89% of the responders described their headache as imploding (extreme pressure outside the head) or ocular (extreme pressure behind the eyeball). We conclude therefore that migraine with imploding or ocular headache was highly associated with successful prevention of attacks using a botulinum toxin type A and that migraine with exploding headache was highly associated with failure to block migraine attacks when a botulinum toxin type A was administered.

Example 4

Selecting Migraine Patients with Ocular Headache Pain versus Exploding Headache Pain for Treatment with Botulinum Toxin Patients have reported symptoms and effects of ocular migraine headache pain as follows: "I want to take a spoon and pull out my eye"; "my eyes are popping out"; "someone is jabbing a knife into my eye and I want to take my eye out", and; "someone is pushing a finger into my eye". A common aspect of ocular headache pain (synonymously ocular migraine headache pain) is a feeling of pain in the eye, or in the eye socket or adjacent tissue. In one prospective, double blind study of patients with migraine which included two patients with ocular headache pain, both these migraine patients with ocular headache pain responded (became headache free) after administration of a botulinum toxin (BOTOX). Additionally, in a second retrospective, triple blind study (blinded as to investigator, patient and attending physician) of patients with migraine which included eight patients with ocular headache pain, all eight of these migraine patients with ocular headache pain responded (became headache free) after administration of a botulinum toxin (BOTOX).

The results from Examples 1-4 can be summarized in FIG. 4 which shows that selecting for migraine patients who have imploding headache pain and/or ocular headache pain, as opposed to exploding headache pain, dramatically reduced the number of days per month, after administration of a botulinum toxin type A (i.e. BOTOX), during which the patients had a migraine headache.

Example 5

Treatment of Migraine with Botulinum Toxin

A female patient, 32 years old complains of migraine headaches. Before botulinum toxin type B administration she suffers about 25 migraine attacks a month, each lasting most of a day with pain intensity of 8 on a scale of 0 to 10.

Based on her pain perception she is classified as having an imploding headache pain. After administration of a botulinum toxin type B (1200 units into the frontals and glabellar muscles, 800 units into the occipitalis muscles and 200 units into the trapezius muscle) she experiences only one migraine attack a month with pain intensity of 1 out of 10.

All references, articles, patents, applications and publications set forth above are incorporated herein by reference in their entireties. Although the present invention has been described in detail with regard to certain preferred methods, other embodiments, versions, and modifications within the scope of the present invention are possible. For example, each of the botulinum neurotoxins A, B, C, D, E, F and G can be effectively used in the methods of the present invention.

Accordingly, the spirit and scope of the following claims should not be limited to the descriptions of the preferred embodiments set forth above.

We claim:

1. A method for treating a headache, the method comprising the steps of:
   (a) selecting a patient by determining that the patient has at least one symptom of an imploding headache pain, wherein the at least one symptom includes a perception of pressure or force exerted from outside of the patient's skull in an inward fashion, a feeling of an object sitting heavy on the patient's head, a feeling of an object squeezing the patient's head, a feeling of a vice being tightened on the patient's head, a feeling of a sharp object being inserted into his head, or combinations thereof; and;
   (b) administering locally a therapeutically effective amount of a botulinum toxin type A to the selected patient, wherein the number of injection sites is 23 to 58, and the therapeutically effective amount ranges from about 105 to about 260 units, thereby treating the headache.

2. The method of claim 1, wherein the headache is a migraine headache.

3. A method for treating a headache, the method comprising the steps of:
   (a) selecting a patient for treatment of a headache by determining that the patient has at least one symptom of an ocular headache pain, wherein the at least one symptom includes a feeling of pain or pressure on or in the eye, the eye socket, adjacent tissue, double vision, visual hallucinations, or combinations thereof, and;
   (b) administering a therapeutically effective amount of the botulinum toxin type A by injection to the selected patient, wherein the number of injection sites is 23 to 58, and the therapeutically effective amount ranges from about 105 to about 260 units, thereby treating the headache.

4. The method of claim 3, wherein the administration is by local administration.

5. The method of claim 3, wherein the headache is a migraine headache.

\* \* \* \* \*